United States Patent [19]

Jannelli

[11] 4,220,402
[45] Sep. 2, 1980

[54] TRIAL LENS EYEGLASS CLIP

[76] Inventor: Gilbert G. Jannelli, c/o St. Luke's Eye Clinic, Aspen and High, New Port Richey, Fla. 33552

[21] Appl. No.: 866,544

[22] Filed: Jan. 3, 1978

[51] Int. Cl.² ............................ A61B 3/04; A61B 3/10
[52] U.S. Cl. .......................................... 351/22; 33/200
[58] Field of Search ........................ 351/21, 19, 22, 20; 33/200

[56] References Cited

U.S. PATENT DOCUMENTS

| 1,717,224 | 6/1929 | King | 351/22 |
| 2,068,103 | 1/1937 | Harris | 33/200 X |

FOREIGN PATENT DOCUMENTS 524822 8/1940 United Kingdom ...................... 351/19

OTHER PUBLICATIONS

Halberg Trial Clip, Keeler, London, England, Jun. 1972.

Primary Examiner—John K. Corbin
Assistant Examiner—Rodney Bovernick
Attorney, Agent, or Firm—Wegner, Stellman, McCord, Wood & Dalton

[57] ABSTRACT

An eyeglass clip for holding trial lenses in selected alignment with an eyeglass lens and being adapted to be attached to a pair of eyeglasses includes a body member defining a contoured rim with a large central aperture and a lens holder extending forwardly therefrom defining a channel with at least three axially spaced grooves formed therein adapted to receive trial lenses, a spring clip holding a trial lens in a fixed position when inserted into one of the grooves, a plastic clip member secured to the rear of the body member which resiliently holds the rim against an eyeglass when the eyeglass is positioned between the rim and the body member, and leveling means for indicating the proper angular orientation of the eyeglass clip on the eyeglasses.

6 Claims, 5 Drawing Figures

TRIAL LENS EYEGLASS CLIP

BACKGROUND OF THE INVENTION

1. Field of the Invention

This invention relates generally to an instrument for testing a patient's eyes and, more particularly, to a clip attachable to a pair of eyeglasses capable of holding a plurality of trial lenses.

2. Description of the Prior Art

A clip of the general type disclosed herein is designed for use in the ophthalmic profession by ophthalmologists, optometrists, opthalmolic assistants primarly for cataract overrefractions and the like. The clip is placed over a pair of eyeglasses that have a lens of a known power. The clip has a grooved lens holder into which trial lenses are added to give a final power. The entire optical system thus generated is measured, thereby giving an indication of the condition of the eyes and enabling a pair of eyeglasses to be made up from the calculations derived from the optical system measurements.

One such clip which has been utilized in the past includes a body member defining a large aperture, a lens holder having a pair of grooves for holding two trial lenses, and a metal clip member including a post secured by screws to the rear surface of the body member and a pair of curved legs covered with rubber tubes and having an operating tab screwed to the post extending angularly upwardly away from the post and rearwardly from the body member. This prior art clip was attached to an eyeglass of a pair of eyeglasses by inserting one eyeglass between the clip member legs and the body member so that the resiliency of the clip member biased the legs against the rear surface of the eyeglass lens and the front surface of the lens was held against the flat rear surface of the body member with the clip aperture lined generally with the eyeglass lens.

While the prior art clip functioned relatively well, there were numerous disadvantages in its use. First, it had no means for orienting the eyeglass clip relative to horizontal so as to properly align the 0°–180° axis line of the angular scale which was formed on the lens holder. Only two trial lenses could be utilized at any one time and because the trial lenses were not held fixedly in place, the trial lenses could move, rock, or rotate, thereby causing a change in setting when the eyeglass clip was removed to the lensometer to be measured. In addition, the metal clip member was subject to accidental bending which could not be satisfactorily rectified so as to return the inherent spring action of the clip member to its original effectiveness in holding the eyeglass clip against the eyeglass lens. Finally, the flat rear surface of the body member did not permit a four-point touch on the curved front surface of the eyeglass lens, and thereby permitted the clip to rock relative to the eyeglass.

SUMMARY OF THE INVENTION

It is a principal object of the invention to provide an improved eyeglass clip which is attachable to a pair of eyeglasses and is capable of holding trial lenses in a satisfactory manner.

One feature of the invention permits the frame of the eyeglasses to be advantageously positioned closer to the apex of the cornea of the eye than was previously possible with the prior eyeglass clip.

Additional features of the invention are the inclusion of a leveling vial to assist in orienting the 0°–180° axis line of the angular scale and an additional groove formed in the lens holder to support an additional trial lens therein.

In accordance with the invention, an eyeglass clip is constructed so as to include a main body member having top and bottom portions, a clip member and a level. The bottom portion defines an annular rim from which the lens holder extends forwardly to define a semicylindrical channel having three grooves defined therein to support three trial lenses. The clip member, which is formed from plastic, is secured to the rear of the main body portion and has legs which extend downwardly and are held adjacent the rim on either side of an aperture defined in the rim by the inherent resiliency of the clip member. The clip member has an upwardly extending operating finger which is directed forwardly towards the main body portion so that it is spaced from the eyebrow of the wearer of the eyeglasses. This permits the frame of the eyeglasses to be moved closer to the eye and, consequently, the trial lenses are also moved closer. Because the clip member is integrally formed from plastic, it will not bend so as to reduce the effectiveness of the resilient holding power of the legs.

In a preferred embodiment of the invention, biasing means, such as a spring clip, is secured to the lens holder and extends slightly into one of the grooves of the lens holder. The biasing member includes a protuberance which permits the biasing member to be deflected out of the groove when a trial lens is inserted therein. However, the inherent resiliency of the biasing member causes the protuberance to be urged into engagement with the lens, thereby holding the lens against the wall of the groove and in frictional engagement therewith so as to maintain the lens in selected position.

The rear surface of the rim of the eyeglass clip surrounding the relatively large aperture is beveled forwardly and inwardly toward the aperture such that the rear surface is contoured so as to generally conform with a convex eyeglass lens thereby providing a four-point contact with the lens when the eyeglass clip is placed thereover and biased thereagainst by the resilient action of the clip member on the back surface of the eyeglass lens.

BRIEF DESCRIPTION OF THE DRAWINGS

The details of construction and operation of the invention are more fully described with reference to the accompanying drawings which form a part hereof and in which like reference numerals refer to like parts throughout.

In the drawings.

DESCRIPTION OF THE PREFERRED EMBODIMENT

Figure 1:
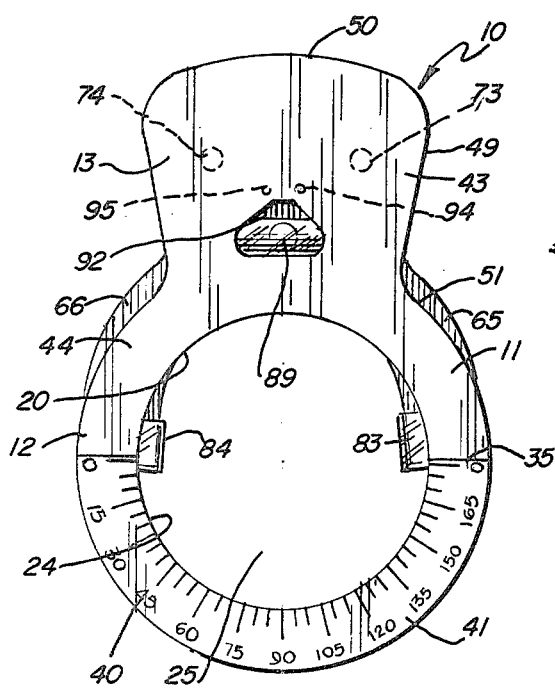
FIG. 1 is a front elevational view of a trial lens eyeglass clip constructed in accordance with the invention.
Figure 4:
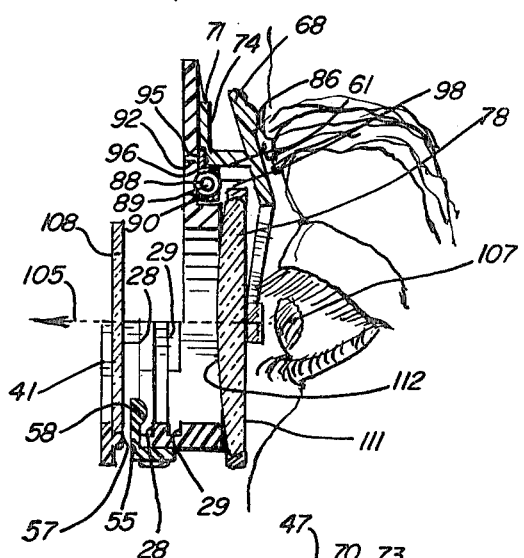
FIG. 4 is a cross-sectional view of the eyeglasses and the eyeglass clip attached thereon showing the axial relationship between the eye of the wearer, the eyeglass lens and the eyeglass clip; and, FIG. 5 is a perspective view of the eyeglass clip shown in FIG. 1 as seen from a position rearwardly and laterally therefrom.
Figure 2:
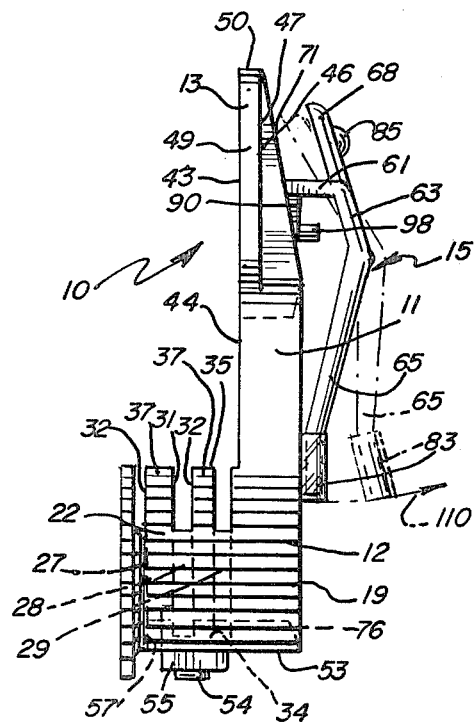
FIG. 2 is a side elevational view of the eyeglass clip shown in FIG. 1 with the deflected position of the clip member shown in phantom.
Figure 5:
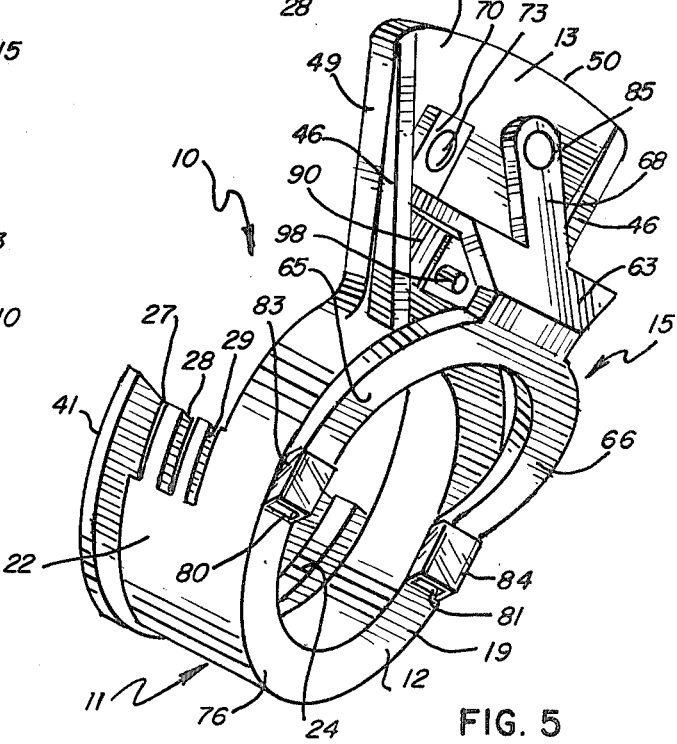

As seen in FIGS. 1, 2 and 4, an eyeglass clip, generally designated 10, for holding trial lenses is seen to broadly include a main body member 11 having bottom and top portions 12 and 13, respectively, a clip member 15, and a level 17. The body member 11 and the clip member 15 are each integrally formed from ABS plastic.

The bottom portion 12, in turn, includes an annular rim 19 defining a relatively large aperture 20 and a trail lens holder 22 disposed below the aperture 20 and extending forwardly from the rim 19. The lens holder 22 has a semicircular cross-sectional configuration with an arcuate internal wall 24 defining an upward-opening semicylindrical channel 25. Formed in the channel wall 24 are axially spaced arcuate grooves 27, 28 and 29, each having forward and rearward walls 31 and 32. The respective groove bottom walls 34 terminate short of the top edge 35 of the lens holder 22 so as to define spaced upward extensions 37.

As seen in FIG. 1, a silk-screened angular scale 40 is formed on a dial face 41 at the front of the lens holder 22. The scale 40 cooperates with a line or arrow juxtaposed on a trail lens (not shown in FIG. 1) placed in the outer groove 27 so as to give a visual indication of the angular position of the lens relative to horizontal. This measurement may be denoted in degrees (0°–180°).

The top portion 13 extends upwardly from the thicker bottom portion 12 and has a front surface 43 coinciding with the front surface 44 of the rim 19. To provide structural strength, ribs 46 are integrally formed on the rear surface 47 of the top portion 13 adjacent each of the lateral edges 49 and extend from the upper edge 50 of the top portion 13 to the upper periphery 51 of the rim 19.

Secured to the lower periphery 53 of the rim 19 by suitable means, such as screw 54, is an L-shaped spring clip or biasing member 55 which extends upwardly through an aperture 57 defined in the bottom wall of the lens holder 22. The biasing member 55 has a rounded protuberance 58 which extends slightly into the intermediate groove 28. When a trial lens (not shown) is inserted downwardly into the intermediate groove 28, the biasing member 55 will be deflected out of the groove 28. However, the inherent resiliency of the biasing member 55 causes the protuberance 58 to be urged into engagement with the trial lens thereby holding the trial lens against the rear wall 32 of the intermediate groove 28 and into frictional engagement therewith so as to maintain the trial lens in selected position.

The clip member 15 generally includes a pair of support posts 60 and 61, a center segment 63, a pair of legs 65 and 66, and an operating tab or finger 68. The laterally spaced support posts 60 and 61 extend rearwardly from the rear surface 47 and each has a respective mounting flange 70 or 71 defining bores (not shown) adapted to receive studs 73 and 74, respectively. The studs 73 and 74 are formed integral with the rear surface 47 and extend rearwardly and outwardly therefrom. The ends of the studs 73 and 74, when the mounting flanges 70 and 71 are placed thereover during assembly, are flattened, as by the application of heat, to rivet the clip member 15 in place on the rear surface 47 between the ribs 46. The center segment 63, which is spaced rearwardly of the rear surface 47, is directed downwardly from the support posts 60 and 61 and rearwardly away from the top portion 13.

The legs 65 and 66, in turn, are directed downwardly from the center segment 63 and forwardly toward the rear surface 76 of the rim 19. The rear surface 76 is contoured or beveled forwardly and radially inward toward the aperture 20 so that it conforms generally to the configuration of a convex lens 78 (FIG. 4) when the eyeglass clip 10 is placed over one of the eyeglass lenses as described in more detail below. The terminal ends 80 and 81 of the respective legs 65 and 66 are angled slightly so as to lie generally parallel to the contoured rear surface 76 of the rim 19 and are covered with plastic vinyl to provide resilient friction pads 83 and 84.

The operating finger 68 extends upwardly from the center segment 63 and forwardly toward the top portion 13 and has a thumb elevation 85 to assist in grasping thereof. As will become more apparent hereafter, the forward angling of the operating finger 68 directs the finger 68 away from the eyebrow 86 (FIG. 4) of the wearer, thereby permitting the eyeglasses upon which the eyeglass clip 10 is attached to be moved closer, i.e., 3–5 millimeters, to the eye or, more specifically, to the apex of the cornea. The molding of the clip makes it possible to reduce the front to rear size of the clip without sacrificing spring action, which reduced size further contributes to permitting the eyeglass to be closer to the eye.

By integrally constructing the clip member 15 from plastic, the spring action is much stronger. This provides a tighter fit between the eyeglasses and the eyeglass clip 10 thereby reducing the probability that the eyeglass clip will move or rock relative to the eyeglasses when attached. Further, the plastic construction is less likely to permanently bend or deform than would a metal construction. Consequently, the eyeglass clip 10 herein described will be operational for a greater length of time.

The level 17 provides an indication of the angular orientation of the eyeglass clip 10 and includes a curved transparent vial 88 with fluid and an air bubble 89 and a plastic housing or enclosure 90 having an open side. A viewing aperture 92 is defined in the top portion 13 of the body member so that the level 17 and housing 90 may be mounted to the rear surface 47 of the top portion 13 between the rim 19 and the support posts 60 and 61. The open side of the housing or enclosure 90 is aligned with the aperture 92 to permit viewing of the location of the bubble 89 relative to a preselected position within the vial 88. The top portion 13 integrally includes a pair of rearwardly directed studs 94 and 95 which pass through bores (not shown) formed in a mounting flange 96 extending from the top of the housing or enclosure 90. The ends of the studs 94 and 95 are flattened during assembly to secure the enclosure 90 in place in a manner similar to that employed to affix the support posts 60 and 61. As a result, the vial 88 is fixed relative to the main body member 10. Studs 98 extend rearwardly from the housing or enclosure 90 to abut the top of the eyeglass frame 102 to assist in aligning the eyeglass clip 10 with the lens axis.

Figure 3:
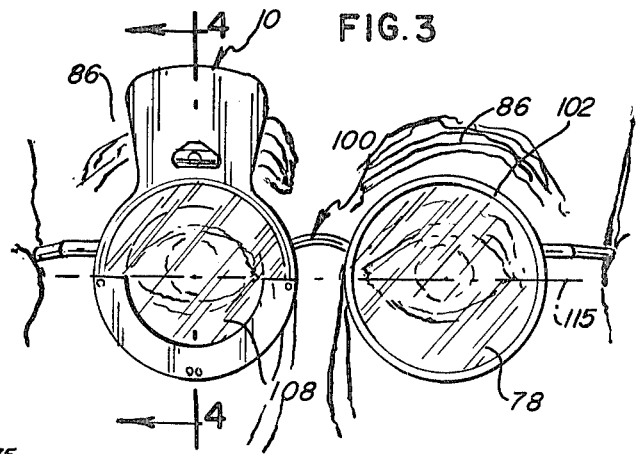
FIG. 3 is a front elevational view of a pair of eyeglasses being worn by a person in which the eyeglass clip shown in FIG. 1 has been attached over one lens.

Referring to FIGS. 3 and 4, the eyeglass clip is shown attached to one lens 78 of a pair of eyeglasses 100 by bridging over the eyeglass frame 102. An eyeglass clip 10 could, of course, be placed over each lens of the eyeglasses. Arrow 105, FIG. 4, indicates the central longitudinal axis of the eyeglass clip. Herein, the eye 107 (specifically, the cornea apex), the center of the lens 78, the center of the aperture 20, and the center of the trial lens 108 are all aligned on the axis 105.

By manually grasping and compressing the top portion 12 and the operating finger 68 together, the legs 65 and 66 will be deflected about the posts 60 and 61 rearwardly away from the rear surface 76 in the direction of the arrow 110 to the phantom position of FIG. 2. The eyeglass clip 10 may then be mounted on the eyeglasses 100 by inserting the frame 102 and lens 78 between the legs 65 and 66 and the rear surface 76 of the rim 19. Upon releasing the operating finger 68, the inherent resiliency of the clip member 15 will cause the legs 65 and 66 thereof to move forward so that the vinyl pads 83 and 84 engage the rear surface 111 of the lens 78 as shown in FIG. 4 and maintain the contoured rear surface 76 in tight four-point contact with the front surface 112 of the lens 78.

When the eyeglass clip 10 is in place, the scale 40 is oriented to a proper angular position by rotating the eyeglass clip 10 relative to the lens 78 until the level 17 indicates a level condition. Various trial lenses, one of which has been shown in outer groove 27 and designated 108 in FIG. 4, may be placed into the grooves 27, 28 and 29 of the lens holder 22. For example, a spherical lens may be placed in the outer groove 27, a cylindrical lens may be placed in the intermediate groove 28 where it is held in position by the biasing member 55, and a maddox rod phoria testing device or prism may be placed in the inner groove 29, all simultaneously if desired. After utilizing a variety of lenses to ascertain the proper correction for a patient, the eyeglass clip 10 is removed and the optical system then present in the lens holder 22 is measured by a lensometer (not shown) which is then added to the known power of the original eyeglass lens to arrive at a final power for the lenses for the patient. The final power can be used to determine the condition of the cornea or can be used to determine the condition of the remainder of the eye.

The eyeglass clip 10 can be used with eyeglasses designed for cataract or aphakic measurement and for overrefraction in cases of myopia (nearsightedness), hyperopia (farsightedness), or astigmatism. The eyeglass clip described herein can also be used for checking bifocals, since the clip may be fitted lower down on a pair of eyeglasses. Proper and accurate checks may be made of both the distance vision and the bifocal vision of the patient with the same clip by merely raising or lowering the position of the eyeglass clip on the eyeglasses relative to the horizontal axis 115, which passes through the center axis 105.

I claim:

1. An eyeglass clip for holding trial lenses in selected alignment with an eyeglass lens and being adapted to be attached to a pair of eyeglasses, comprising:

a body member having a top portion and a bottom portion defining a rim with a relatively large aperture and a lens holder generally forward and below the aperture, said lens holder extending forwardly from said rim and defining a generally semicylindrical channel with at least three axially spaced grooves formed therein adapted to receive trial lenses, said top portion having a relatively small aperture therethrough spaced upwardly from said large aperture;

retaining means associated with at least one of said grooves to hold a trial lens in fixed position against one axial face of the groove when inserted into the associated groove;

an integrally formed plastic clip member secured to the rear of the top portion and having legs extending downwardly one on either side of the large aperture with the ends thereof adjacent the rear of said rim, the inherent resiliency of said clip member biasing said legs forwardly toward said rim to grip the lens of a pair of eyeglasses placed between the rim and the legs;

an operating finger on said clip member extending upwardly away from said clip member and extending forwardly toward said body member with the operating finger directed away from the eyebrow of a person wearing the eyeglasses to permit the eyeglasses to be moved closer to the eye; and leveling means secured to said top portion in alignment with said small aperture for indicating the proper angular orientation of said eyeglass clip on the eyeglasses.

2. The eyeglass clip of claim 1 wherein said retaining means is a spring clip secured to said body member and includes a protuberance extending axially into the groove, the spring clip deflecting out of the groove when a trial lens is inserted into the groove and the inherent resiliency thereof biasing the protuberance into frictional contact with one face of the lens to maintain the lens in selected position.

3. The eyeglass clip of claim 1 wherein said clip member integrally includes a support post secured to the rear of said top portion and extending rearwardly therefrom with the legs being carried by said post at a position spaced from the rear of the top portion and said operating finger extending upwardly from said post and said legs whereby movement of the finger forwardly relative to the body member deflects the legs and the post to move the legs rearwardly away from the rim so that the eyeglasses may be inserted between the body member and the legs, the inherent resiliency of the clip member thereafter fixedly maintaining the eyeglass clip on the eyeglasses.

4. The eyeglass clip of claim 1 wherein the rear surface of said rim is beveled forwardly and radially inward toward the large aperture so that the rim will conform generally to the surface of a convex lens against which it may be held by the clip member to provide greater surface contact between the rim and the lens.

5. The eyeglass clip of claim 1 wherein said leveling means comprises a transparent vial having fluid and a bubble, said bubble moving to a preselected position within said vial when the eyeglass clip is properly oriented relative to horizontal.

6. The eyeglass clip of claim 1 wherein the end of each of said legs is provided with a vinyl pad so that resilient frictional contact may be made with the lens of the eyeglass to which the eyeglass clip is attached.

* * * * *